United States Patent [19]
Jackson et al.

[11] Patent Number: 5,340,541
[45] Date of Patent: Aug. 23, 1994

[54] AUTOMATED KARL FISCHER TITRATION APPARATUS AND METHOD

[75] Inventors: David A. Jackson, Fishers; Ralph M. Riggin; John K. Towns, both of Indianapolis, all of Ind.

[73] Assignee: Eli Lilly and Company, Indianapolis, Ind.

[21] Appl. No.: 27,254

[22] Filed: Mar. 5, 1993

[51] Int. Cl.[5] .................. G01N 31/16; G01N 33/18
[52] U.S. Cl. ......................... 422/75; 204/153.22; 422/81; 436/42; 436/51
[58] Field of Search ............. 422/63, 64, 67, 68.1, 422/75, 100, 103, 104, 81; 436/42, 51; 204/153.22

[56] References Cited

U.S. PATENT DOCUMENTS

| | | | |
|---|---|---|---|
| 3,186,800 | 6/1965 | Strickler | 422/64 |
| 4,005,983 | 2/1977 | Dahms | 436/42 |
| 4,351,799 | 9/1982 | Gross et al. | 422/63 |
| 4,710,355 | 12/1987 | Ushikubo | 422/100 |
| 4,713,974 | 12/1987 | Stone | 73/864.23 |
| 4,749,552 | 6/1988 | Sakisako et al. | 422/75 |
| 4,929,314 | 5/1990 | Simonson et al. | 204/153.23 |
| 4,968,425 | 11/1990 | Morita | 210/488 |
| 5,089,230 | 2/1992 | Kondo et al. | 422/64 |
| 5,179,024 | 1/1993 | Dahms | 436/42 |

OTHER PUBLICATIONS

"Guideline for the Determination of Residual Moisture in Dried Biological Products," Center for Biologics Evaluation and Research, Division of Biochemistry and Biophysics, Laboratory of Analytical Chemistry (HFB-740), Food and Drug Administration, Jan. 1990, Docket No. 89D-0140, pp. 1–10.

M. J. Pikal, K. M. Dellerman, M. L. Roy, and R. M. Riggin, "The Effects of Formulation Variables on the Stability of Freeze-Dried Human Growth Hormone," *Pharmaceutical Research*, vol. 8, No. 4, 1991, pp. 427–436.

S. K. MacLeod, "Moisture Determination Using Karl Fischer Titrations," *Anal. Chem.*, 1991, 63(10) pp. 557–566.

M. J. Pikal, K. Dellerman, and M. L. Roy, "Formulation and Stability of Freeze-Dried Proteins: Effects of Moisture and Oxygen on the Stability of Freeze-Dried Formulations of Human Growth Hormone," *Develop. Biol. Standard*, vol. 74, 1991, pp. 21–38.

(List continued on next page.)

Primary Examiner—Robert J. Warden
Assistant Examiner—Robert Carpenter
Attorney, Agent, or Firm—Woodard, Emhardt, Naughton, Moriarty & McNett

[57] ABSTRACT

Automation of the coulometric Karl Fischer titration has allowed for the accurate, precise determination of moisture content of lyophilized hGH formulations. The system of the present invention utilizes a vented, two-hole sampling/dispensing probe that dispenses titrant and withdraws sample solution through the closed container rubber septum into the Karl Fischer titration reaction vessel. This approach eliminates erroneous results due to environmental moisture contamination or loss of material during the sample transfer process. The system of the present invention is also equipped with a fixed loop valving system, which facilitates the precise measurement of a defined amount of water as a standard. This allows for an accurate accessment of system suitability that was lacking with commercial water standards due to inaccurate moisture content presumably from moisture contamination of the standard under storage and/or at the time of manufacture. The use of the automated system of the present invention has led to a more complete understanding of the role of moisture content on hGH stability and this technology is applicable to other pharmaceuticals where an accurate moisture content determination is needed.

4 Claims, 6 Drawing Sheets

OTHER PUBLICATIONS

I. Nordin-Andersson and A. Cedergren, "Coulometric Determination of Trace Water in Active Carbonyl Compounds Using Modified Karl Fischer Reagents," *Anal. Chem.*, 1987, 59, pp. 749–753.

E. Scholz, "Karl Fischer Titrations of Aldehydes and Ketones," *Anal. Chem.*, 1985, 57, pp. 2965–2971.

T. H. Beasley, Sr., H. W. Ziegler, R. L. Charles, and P. King, "Critical Evaluation of the Karl Fischer Water Method, End-Point Detection System, and Standardization," *Anal. Chem.*, 1972, 44(11), pp. 1833–1840.

M. S. Bloomfield, G. E. Williaams, and R. Jones, "The Determination of Small Quantities of Water in Single Vials of Pharmaceutical Products by Flow Injection Analysis," *Journal of Pharmaceutical & Biomedical Analysis*, vol. 8, Nos. 8–12, 1990, pp. 995–998.

E. E. Theimer and J. J. Pavelek, "Titration of Residual Moisture in Lyophilized Vials," *Journal of Pharmaceutical Sciences*, vol. 57, No. 5, 1968, pp. 887–889.

J. P. H. Wekx and J. P. de Kleijn, "The Determination of Water in Freeze Dried Pharmaceutical Products by Performing the Karl Fischer Titration in the Glass Container Itself," *Drug Development and Industrial Pharmacy*, 16(9), 1990, pp. 1465–1472.

AUTOMATED KARL FISCHER TITRATION APPARATUS AND METHOD

BACKGROUND OF THE INVENTION

Many protein products are freeze-dried to provide adequate shelf life stability. M. J. Pikal, K. M. Dellerman, M. L. Roy and R. M. Riggin, *Pharmaceutical Research* 1990, 8(4), 427–436. To be successful, a freeze-dried product survive processing and storage over the claimed shell life without excessive loss of potency or excessive increase in the level of decomposition products. Human growth hormone (hGH) is an example of a protein that may be freeze-dried without significant degradation, but the resulting solid is potentially unstable. M.J. Pikal, K. M. Dellerman and M. L. Roy, *Develop. biol. Standard*, 1991, 74, 21–38.

Protein stability is more complex in heterogeneous systems such as protein formulations, with the extent of the stability problem being sensitive to both formulation variables and the level of residual water in the freeze-dried solid. Water content can vary depending on the freeze-drying process, and may increase during storage. M.J. Pikal and S. Shah, *Develop. biol. Standard*, 1991, 74, 165–179. Moreover, low residual moisture after manufacture does not ensure low moisture content throughout the shelf life of the product. Freeze-drying of pharmaceuticals for parenteral use is generally performed in the final container, such as a glass ampule or vial. The rubber stoppers typically used to seal the final containers contain a measurable quantity of water, which can transfer to the freeze-dried product until the water content in the product eventually reaches equilibrium with the water content in the stopper.

A low residual moisture content in a freeze-dried protein product is essential to maintain the stability of compounds that are prone to hydrolysis. High water content may decrease protein stability via several mechanisms. The effect of water content and/or water activity on the solid state stability of proteins results from either changes in dynamic activity or conformational stability of the protein, or participation of water as a reactant or medium for mobilization of reactants. Chemical modification generally results in changes to the primary sequence and may or may not have a subsequent effect on conformational structure. Water is a reactant in the deamidation reaction, and high levels of water should increase the rate of deamidation. M. J. Hageman, *Drug Dev. Ind. Pharm.*, 1988, 14, 2047–2070. Residual water in excess of monolayer coverage also increases molecular mobility in the solid protein, thereby increasing general reactivity.

Due to the key role water content plays in the solid state of protein formulations, an accurate and precise moisture determination method is essential in resolving stability issues and in setting specifications and criteria for acceptable moisture content. A number of chromatographic, spectroscopic, electronic, thermal, and wet chemical methods have been used in the past to determine moisture levels. S. K. MacLeod, *Anal. Chem.*, 1991, 63, 557A–565A. The most common of these are loss on drying (LOD), thermogravimetric analysis (TGA), gas chromatography using a thermal conductivity detector, and the Karl Fischer titration.

Of these most common water content measurements, however, the Karl Fischer titration has become the method of choice and is now the approach most widely used in the determination of water content. The direct titration of, or assay for, water using KF reagent is currently in all of the official compendia, and is implied in several official methods manuals (i.e., USP, EP). The titration can be run in either protic or aprotic medium, with the protic medium seeing wider use due to higher sensitivity of the titer to sample and solvent composition. M. S. Kamat, R. A. Lodder and P. P. DeLuca, *Pharmaceutical Research*, 1989 6(11) 961–965. The reaction in protic media (i.e., alcohol) involves sulfur dioxide reacting with the alcohol to produce an alkyl sulfite in a buffered medium using an appropriate base to maintain the solution at the optimal pH. In a coulometric experiment, the iodine is generated electrically from iodine present in the cell The electric efficiency of this method is generally 100%, and the amount of water in the sample is calculated from the number of moles of electrons used in the iodine generation.

An important point to consider with the Karl Fischer titration is the possibility of erroneous results due to water contamination. Titration of small quantities of water in coulometric systems requires a correction for atmospheric moisture entering the system. Sample handling can have a significant impact on the results of a titration as a result of the gain or loss of moisture between sampling and analysis. This leads, at times, to erroneous conclusions because, for example, many lyophilized samples with extreme hygroscopicity pick up atmospheric moisture during sample handling. This becomes increasingly frustrating when one considers the increased variability of the assay due to wide fluctuations in relative humidity throughout the year. Precision in the method is governed largely by the extent to which atmospheric moisture is excluded from the system and the sample.

Accurate moisture content determination measurements using the Karl Fischer titration is contingent on the proper working order of the titration instrument and the chemical reactions. Successful moisture content determinations require 1) that equipment be in proper working order, 2) that reagents be stable and not depleted, 3) that moisture be excluded from the system, 4) that the anodic reaction produce 100% current yield, 5) that the cathodic reaction does not interfere with the titration, and 6) that the reaction not be adversely affected by the sample matrix. To assure that these criteria are being met, the quality of the analysis is checked against standards containing a known moisture content. The correct moisture content determination for the standards confirms that the Karl Fischer titration analysis is running properly, or indicates that a problem exists. A variety of materials have been proposed as standards for moisture content determinations. The principal requirements of these materials are 1) that they contain a stoichiometric amount of moisture that is stable over a wide range of temperature and humidity, 2) solubility in the Karl Fischer titration reagents, 3) ease of handling and storage, 4) availability, and 5) uniformity. M. S. Kamat, R. A. Lodder and P. P. DeLuca, Pharmaceutical Research, 1989, 6(11), 961–965.

Much effort has been given to making liquid water standard solutions less hygroscopic. These efforts have not been completely successful as the water content of the solutions change after the septum over the solutions has been pierced several times. Water is a very good calibration reagent, but it is difficult to accurately dispense liquid water into the Karl Fischer titrator. When delivered by volume, the inaccuracies of the small amount delivered makes it difficult to obtain an accurate value. A more accurate measurement is obtained when the liquid water is delivered by weight, but this again presents difficulties in dispensing the water into the titrator.

Solid water standards have many useful characteristics, but solids such as sodium tartrate dihydrate are not easily dissolved in many Karl Fischer titration reagents, E. Scholz, *Karl Fischer Titration-Determination of Water-Chemical Laboratory Practice*, Springer-Verlag, N.Y. 1984, and questions regarding uniformity of supplies have been raised. T. H. Beasley, H. W. Siegler, R. L. Charles and P. King, *Anal. Chem.*, 1972, 44, 1833-1840. It has been observed that the moisture content value of the Hydrahal ® solid standard (sodium tartrate dihydrate) varied widely depending from where the sample is taken within the sample container. Sampling from the top of the bulk material (skimming the top) resulted in moisture content values approximately 15% less than the expected value and 10% less than the average value of samples taken deeper in the container. The UpJohn Company has found that a lincomycin hydrochloride monohydrate standard does not change water content over a wide range of relative humidities, and is quite stable. The availability of this material, however, is unclear because it is a prescription pharmaceutical. M. S. Kamat, R. A. Lodder and P. P. DeLuca, *Pharmaceutical Research*, 1989, 6(11), 961-965.

Due to the foregoing concerns regarding sample handling and accurate water standard determinations, the usefulness of coulometric moisture determinations as currently performed in measuring residual moisture is questionable. This is no better demonstrated than in the analysis of formulations of human growth hormone in vials and cartridges. The stability of this product is adversely affected by high moisture content in the lyophilized plug and is quickly affected by environmental moisture contamination upon exposure to the laboratory atmosphere. In the past, the vialed material was weighed on a balance, the rubber stopper removed, the lyophilized plug broken up into a powder with a spatula, the contents dispensed into the titrator using a glass funnel, the rubber stopper placed back on the vial, and the vial reweighed on the balance. The difference in weight was punched into the Karl Fischer titrator to be used for the percent moisture content value.

The time to transfer the material, from the time of removing the rubber stopper to the time of dispensing the entire contents of the vial, depended on how adept the operator was in performing the transfer. The faster the transfer, the less exposure to the lab atmosphere, and the less moisture content contamination. This is well illustrated in FIG. 6, which shows the dramatic effect of transfer time on moisture content values for a 5 mg formulated vial of hGH at a laboratory relative humidity level of 40%. The fastest one of the inventors, with several months experience, was able to transfer the contents of the vial into the reaction vessel in 28 seconds. Transfer times greater than this minimum transfer time resulted in a sharp increase in moisture content, with a doubling of the transfer time resulting in a 125% increase in moisture content for this material. Transfer times greater than approximately one minute resulted in little increase in moisture content, indicating an equilibrium with the laboratory atmosphere.

This data raised the question of the extent of moisture contamination prior to the 28 second minimum transfer time. One can assume that moisture contamination is occurring as soon as the rubber stopper is removed from the vial. This measured moisture content value therefore has little correlation to the actual moisture content in a closed vial due to the physical limitations of this material transfer process. This prior art process is confounded further by the fact that the relative humidity in a lab typically varies from day to day and from month to month. The relative humidity in the inventors' laboratory has varied from 15% to 50% during a one month period.

Another problem with the sample transfer process of the prior art is dispensing the lyophilized material into the Karl Fischer titrator. The material is rather flaky, and when trying to pour the material through the funnel, some material is lost into the atmosphere. The material also adheres to the sampling funnel and is not all dispensed into the titrator. To get around this, weighing paper can be rolled to crate a funnel, but this takes some operator dexterity, during which the titrator is open to the atmosphere. In its prior art configuration, Karl Fischer titrations of hGH formulations were affected by: 1) sample transfer time, 2) relative humidity in the laboratory, and 3) material lost in the material transfer. These factors make it impossible to determine the accurate moisture content in the closed vial.

SUMMARY OF THE INVENTION

The aim of the present invention is to improve the conditions for trace water determinations by automating the coulometric Karl Fischer titration. Automation of the coulometric Karl Fischer titration has allowed for the accurate, precise determination of moisture content of lyophilized hGH formulations by minimizing tile exposure of the formulation samples to the external environment and by eliminating sample transfer errors. The preferred embodiment of the present invention utilizes a vented sampling/dispensing probe that punctures the original sample container's rubber septum, dispenses titrant to dissolve the sample in its original container, and then withdraws the dissolved sample from the closed sample container and deposits the dissolved sample into a Karl Fischer titration reaction vessel. In the preferred embodiment to date, the instrumentation and other components of the automated Karl Fischer titration devices of the present invention are enclosed within a controlled environment with low relative humidity. This approach further eliminates erroneous results due to environmental moisture contamination.

The preferred embodiment of the present invention is also equipped with a fixed loop valving system that facilitates the precise moisture measurement of a defined amount of liquid water. This allows for an accurate accessment of system suitability that has been lacking with tile unreliable commercial water standards of the prior art due to the moisture contamination of the present commercial water standards under storage or at the time of analysis, and/or at the time of manufacture.

The use of the automated system of the present invention has led to a more complete understanding of the role of moisture content on hGH formulations stability. The automated system of the present invention makes it possible to more accurately measure the moisture content of a wide variety of sample containers and sample amounts. Although the preferred embodiment of the present invention focuses on the determination of the moisture content of hGH formulations, the automated Karl Fischer titration system of the present invention can be used to determine the moisture content of any sample that can be solubilized in the Karl Fischer titrant.

Automation of the coulometric Karl Fischer titration according to the present invention has overcome the following well-known problems of the prior art instruments and processes: 1) moisture contamination from the atmosphere, 2) loss of sample material during dispensing, 3) inaccurate weighing of sample material being dispensed, and 4) unreliable commercial water standards.

One embodiment of the present invention is an apparatus for automated coulometric determinations of moisture content using a Karl Fischer titrator, comprising a Karl Fischer titrator having a reaction vessel containing titrant; an autosampler having a sample rack for receiving sealed sample containers containing titrant soluble samples, sampling/dispensing probe means for piercing sealed sample containers and communicating titrant to and sample/titrant solutions from within sealed sample containers, an automated 3-way valve means in fluid communication with the reaction vessel of the Karl Fischer titrator, a sample/titrant reservoir, and tile sampling/dispensing probe means, for directing the flow of fluids alternatively between the sampling/dispensing probe and the sample/titrant reservoir, and between the sample/titrant reservoir and the reaction vessel of the Karl Fischer titrator; a first automated syringe pump in fluid communication alternatively with the sample/titrant reservoir, and the reaction vessel of the Karl Fischer titrator; automated 4-port injection valve means in fluid communication with the reaction vessel of the Karl Fischer titrator, and including a microliter loop of predetermined volume, for directing the flow of titrant through the microliter loop alternatively to or from the reaction vessel of the Karl Fischer titrator and to a waste reservoir, and for directing the flow of a liquid water standard alternatively from a liquid water standard source to the microliter loop and froin the microliter loop to the reaction vessel of the Karl Fischer titrator; a second automated syringe pump in fluid communication with the microliter loop of the automated 4-port injection valve means and with a water standard source; a third automated syringe pump in fluid communication with the reaction vessel of the Karl Fischer titrator through the microliter loop of the automated 4-port injection valve means, and alternatively, a waste reservoir; and computer means for controlling and coordinating the operations of the Karl Fischer titrator, the autosampler, the automated 4-port injection valve means, and the first, second and third automated syringe pumps.

Another embodiment of the present invention is an apparatus for automated coulometric determinations of moisture content using a Karl Fischer titrator, comprising a Karl Fischer titrator having a reaction vessel containing titrant; an autosampler having a sample rack for receiving sealed sample containers containing titrant soluble samples, sampling/dispensing probe means for piercing sealed sample containers placed in the sample rack and communicating titrant to and sample/titrant solutions from within sealed sample containers, and automated 3-way valve means in fluid communication with the reaction vessel of the Karl Fischer titrator, a sample/titrant reservoir, and the sampling/dispensing probe means, for directing the flow of fluids alternatively between the sampling/dispensing probe and the sample/titrant reservoir, and between the sample/titrant reservoir and the reaction vessel of the Karl Fischer titrator; a first automated syringe pump in fluid communication with the sample/titrant reservoir, and alternatively, the reaction vessel of the Karl Fischer titrator; computer means for controlling and coordinating the operations of the Karl Fischer titrator, the autosampler, and the first automated syringe pump.

Another embodiment of the present invention is an apparatus for coulometric determination of the moisture content of a liquid water standard for a Karl Fischer titrator having a reaction vessel containing titrate, comprising automated 4-port injection valve means in fluid communication with the reaction vessel of the Karl Fischer titrator, and including a microliter loop of predetermined volume, for directing the flow of titrant through the microliter loop alternatively to or from the reaction vessel of the Karl Fischer titrator, and to a waste reservoir, and for directing the flow of a liquid water standard alternatively from a liquid water standard source to the microliter loop and from the microliter loop to the reaction vessel of the Karl Fischer titrator; a first automated syringe pump in fluid communication with the microliter loop of the automated 4-port injection valve means and with a water standard source; a second automated syringe pump in fluid communication with the reaction vessel of the Karl Fischer titrator through the microliter loop of the automated 4-port injection valve means, and alternatively, with a waste reservoir.

Another embodiment of the present invention is a process for coulometric determination of moisture content using a Karl Fischer titrator, comprising the steps of providing a Karl Fischer titrator having a reaction vessel containing titrant, and a sealed sample container containing a sample that is soluble in the titrant, piercing the sealed sample container with a substantially moisture free, vented sampling/dispensing probe having probe holes that are in fluid communication with the reaction vessel, communicating titrant from the reaction vessel through the probe holes to within the sealed container, withdrawing sample/titrant solution from the sealed container through the probe holes, and communicating the sample/titrant solution to the reaction vessel for coulometric determination of moisture content.

Another embodiment of the present invention is a process for coulometric determination of moisture content of a liquid water standard for a Karl Fischer titrator, comprising the steps of providing a Karl Fischer titrator having a reaction vessel containing titrant, and a microliter loop of predetermined volume in fluid communication with the reaction vessel, and alternatively, a liquid water standard source and a titrant source, filling the microliter loop with water from the liquid water standard source, and injecting the liquid water standard within the microliter loop from the microliter loop into the reaction vessel with titrant from the titrant source for coulometric determination of the moisture content of the liquid water standard from within the microliter loop.

Related objects and advantages of the automated Karl Fischer titration apparatus and process will be evident from the following detailed description.

DESCRIPTION OF THE PREFERRED EMBODIMENTS

Figure 1:
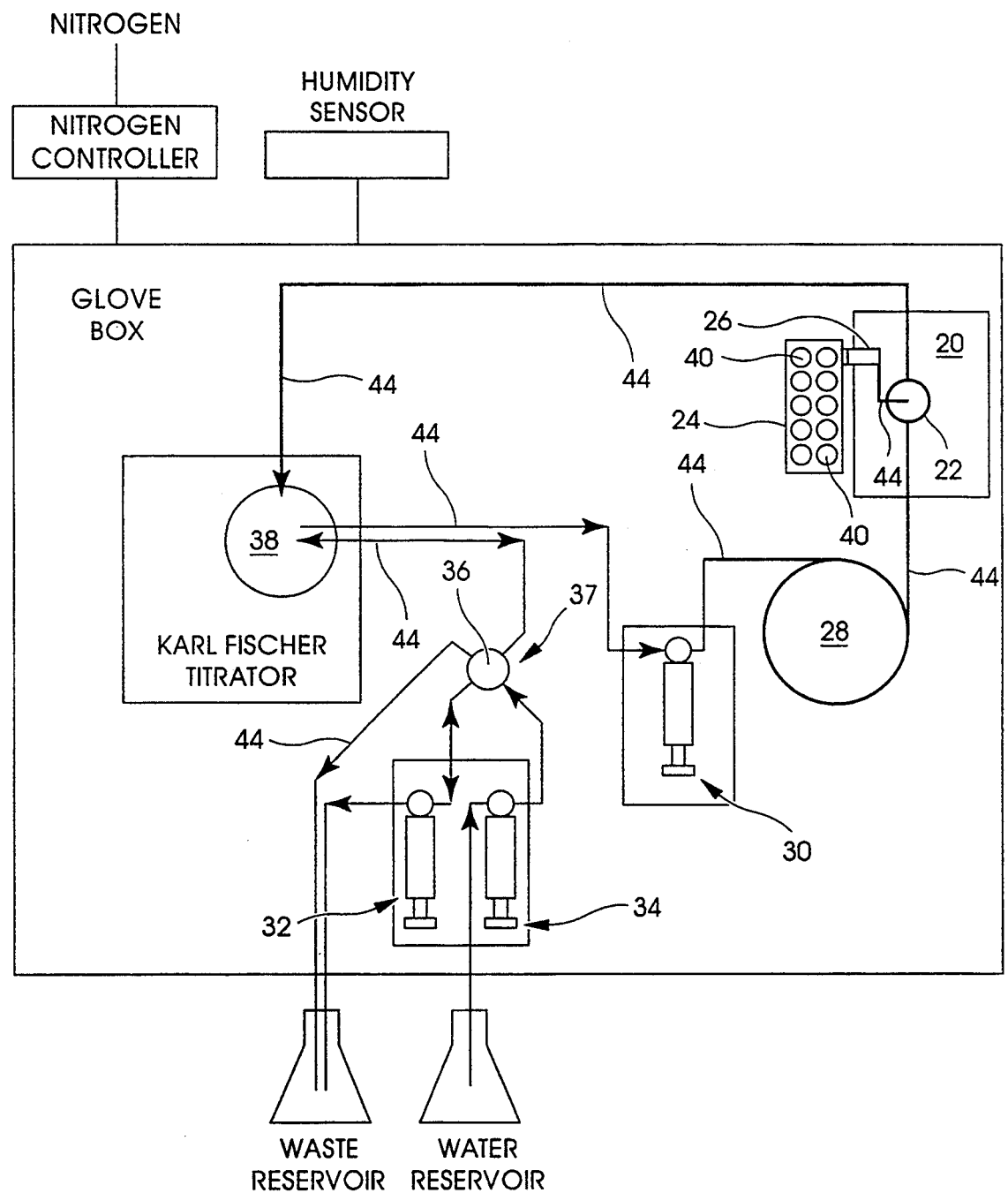
FIG. 1 is a schematic diagram of a preferred embodiment of the apparatus and process of the present invention as applied to the determination of moisture content of hGH formulations.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated apparatus and process, and such further applications of the principles of the invention as illustrated therein being contemplated as would normally occur to one skilled in the art to which the invention relates.

Instrumentation

Figure 2:
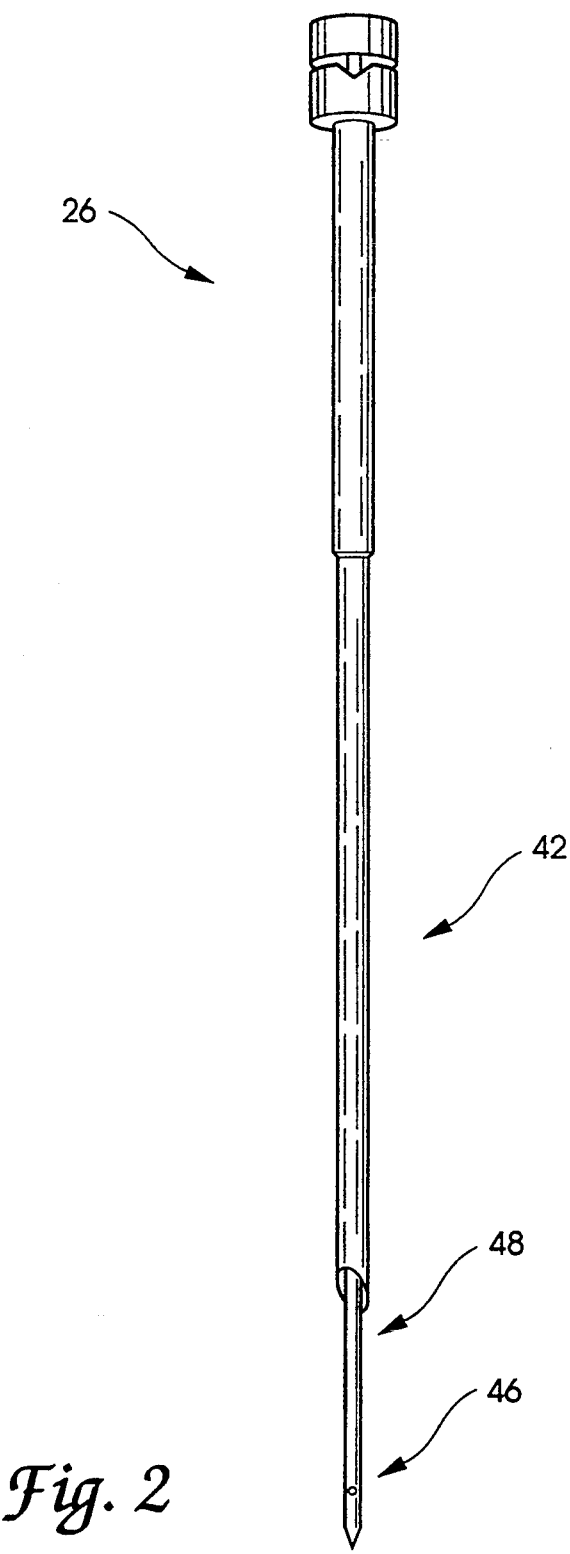
FIG. 2 is an elevational view of the probe of the apparatus of FIG. 1.
Figure 3:
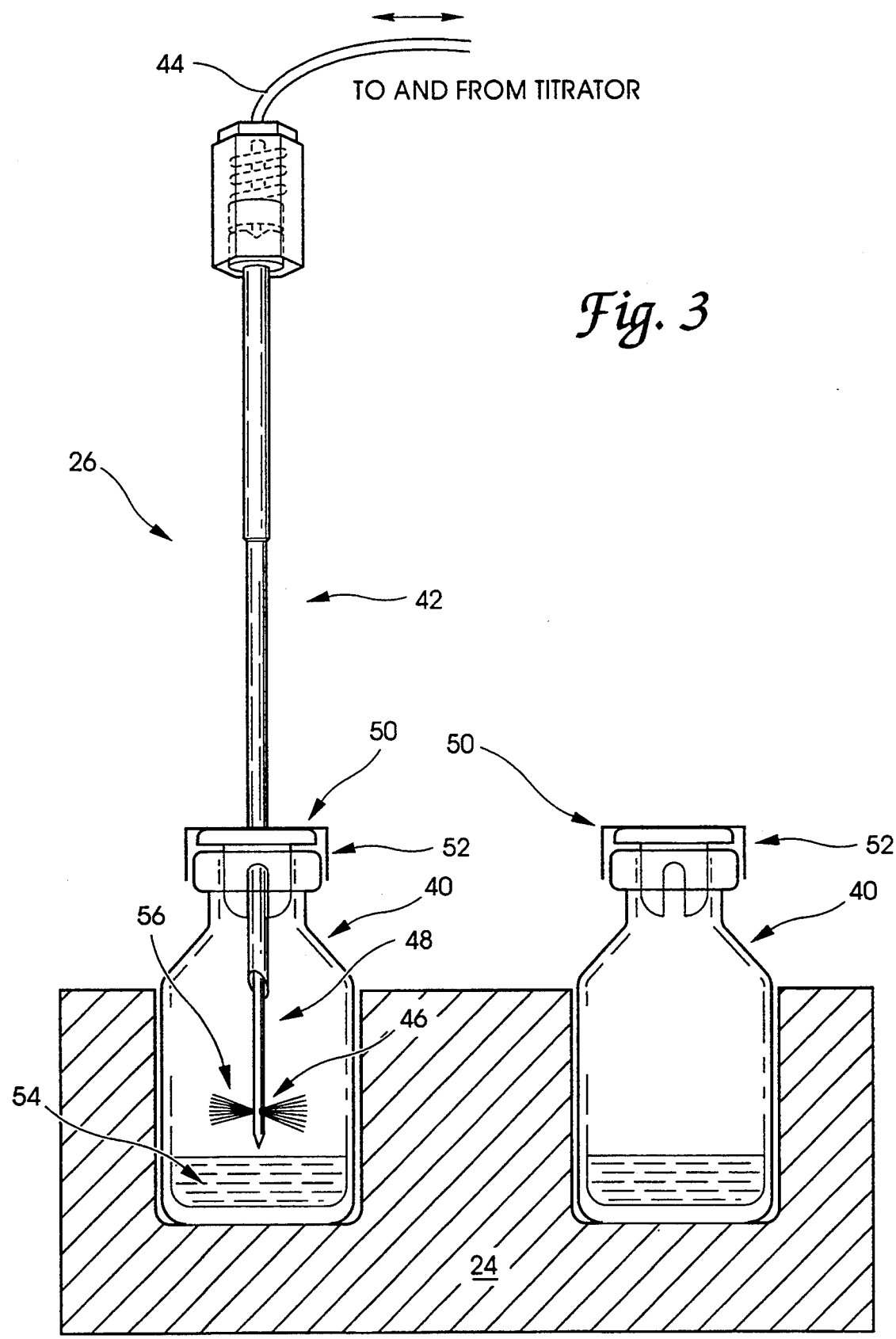
FIG. 3 is an enlarged and partially segmented view of probe and sample rack of FIG. 1 shown with exemplary sample vials.

Referring now to the drawings, the instrumentation and other components of the preferred embodiment of the present invention are illustrated in FIGS. 1–3. FIG. 1 diagrams the hardware of the preferred embodiment and the movement of fluids through the system. The bold lines in FIG. 1 represent the paths taken by dissolved samples. An encapsulating glove box utilized in the preferred embodiment (35"W×24"D×20"H) is constructed of hermetically sealed static dissipative PVC (Terra Universal Inc., Anaheim, CA). Shown in FIG. 1 are the preferred gas control units, a Dual Purge System and a Nitrowatch (both from Terra Universal, Inc., Anaheim, CA), which control the flow of dry nitrogen (house) into the glove box. Within the glove box, sample vials 40 are placed into a sample rack 24 that is customized for specific sizes of sample vials 40 (FIG. 3). The sample rack 24 screws into a bar on an autosampler 20 (Model 221, Gilson Medical Electronics, Inc., Middleton, WI). Mounted on top of the autosampler 20 is a 3-way valve 22 (Bio-Chem Valve Corp., East Hanover, NJ) that will direct the flow of titrant and dissolved samples to either the sample vials 40 through a probe assembly 26 (Popper & Sons, Inc., New Hyde Park, NY), or to a sample/titrant reservoir 28, or to the reaction vessel 38 of a Karl Fischer titrator (Model CA-06, Mitsubishi, Norwood, NJ). Dried coulomat solution (titrant) 56 (FIG. 3) is introduced to the sample vials 40 through two 0.5 mm probe holes 46 in the sampling/dispensing probe 48 of the probe assembly 26 as illustrated in FIG. 3. The outer tube portion of the probe assembly 26 serves as a vent tube 42 to vent a sample vial 40 when it is punctured by the sampling/dispensing probe 46 (FIG. 3). In the preferred embodiment to date, there are two lengths of vent tubes 42, a 90 mm length for sample vials 40 and 70 mm for cartridges (not shown).

Teflon tubing 44, 1/16" I.D., is used for transfer tubing between the probe assembly 26, the 3-way valve 22, the Karl Fischer titrator and an automated titrant syringe pump 30 (Micro-Lab 900, Hamilton Company, Reno, NV), and to construct a sample reservoir 28 from loops of tubing between the 3-way valve 22 and the titrant/sample syringe pump 30.

Referring again to FIG. 1, correct operation of the Karl Fischer titrator is ascertained through the testing of the moisture content of a known amount of liquid water. The instrumentation of the preferred embodiment for testing the Karl Fischer titrator with a liquid water standard includes a rotating 4-port injection valve 36 (Model 7410, Rheodyne Inc., Cotati, CA, with a valve actuator Model 732, Alcott Chromatography, Norcross, GA) with a 9.5 microliter loop 37 (Rheodyne Inc., Cotati, CA). The injection valve 36 rotates and the 0.5 microliter loop 37 is filled with distilled water drawn from a water reservoir using an automated water standard syringe pump 34 (Micro-Lab 900). The injection valve 36 rotates again and the distilled water within the fixed loop 37 is flushed into the reaction vessel 38 of the Karl Fischer titrator using titrant from an automated titrant syringe pump 32 (Micro-Lab 900). Teflon tubing 44, 1/16" I.D., is also used between the 4-port injection valve 36 with a 0.5 microliter loop 37, the Karl Fischer titrator, the syringe pumps 32 and 34, and waste and water reservoirs outside the glove box, as illustrated in FIG. 1.

In the preferred embodiment to date, all operations of the automated Karl Fischer titration apparatus are controlled through software written in QBASIC, running on a CompuAdd computer (Model 333LP, CompuAdd, Austin, TX). Two addition boards were installed in the computer. One of these (PDISO-8, Metrabyte) contains relays that operate the 3-way valve 22 and the injection valve 36 actuator. The other board (KW-509B, Microtek) is a communications board with two additional RS232 serial ports. The preferred QBASIC software to date for the automated Karl Fischer titration apparatus of the preferred embodiment is appended to the end of the Description of the Preferred Embodiments.

Reagents

Hydranal ® Coulomat C (Riedel-de Haen) was used in the cathodic compartment of the Karl Fischer titrator's reaction vessel 38. Various mixtures of Hydranal ® Coulomat A or AG (Riedel-de Haen) and formamide (EM Science) were used in the anodic compartment of the reaction vessel 38.

Operation

The determination of the moisture content of a water standard and of a sample is described below with respect to the instrumentation and other components of the preferred embodiment diagrammed in FIGS. 1–3. To start the analysis, the house nitrogen valve was opened and the flow of nitrogen into the glove box was regulated by the nitrogen controller until a set relative humidity was indicated by the humidity sensor (hygrometer). The system was ready for use when the relative humidity inside the glove box reached about 5%. An appropriately sized sample rack 24 was fitted onto the autosampler 20 with set screws, and the selected sample vials 40 were loaded into the sample rack 24. The computer program was initiated through the computer by selecting the titration option from the menu where a series of questions were posed to the operator concerning the container size, number, and identification of samples 40. After the appropriate parameters were entered into the computer, a water standard was processed.

The first step in processing a water standard was the removal of any moisture in the associated tubing and titrant syringe pump 32. This is a two step procedure in the preferred embodiment. The first step is the flushing of the titrant syringe pump 32 twice with 3 ml of titrant from the reaction vessel 38 on the Karl Fischer titrator. Following each flushing, the titrant is pushed by syringe pump 32 to the waste reservoir located outside the glove box. The second step is the flushing of the transfer lines, which is accomplished by drawing titrant from the reaction vessel 38 into the transfer tubing, through the injection valve 36 and into the titrant syringe pump 32. The titrant is then pushed back into the reaction vessel 38 of the Karl Fischer titrator by titrant syringe pump 32, and a moisture measurement is taken. If the response is greater than 8.0 micrograms of water, the second step of the rinsing procedure is repeated and is continued until the response is less than 8.0 micrograms.

When the moisture level is less than the 8.0 micrograms cutoff, titrant syringe pump 32 is filled with titrant from the reaction vessel 38 and water standard syringe pump 34 is filled with distilled water from the water reservoir located outside the glove box. The injection valve 36 is rotated to a "load" position and the 0.5 microliter loop 37 is filled with water from water standard syringe pump 34. The injection valve 36 then rotates back to an "inject" position and syringe pump 32 containing titrant carries the 0.5 microliters of water from the 0.5 microliter loop 37 into the reaction vessel 38 of the titrator for measurement. If the moisture content value of the standard falls outside the system suitability range, then the old reagents are replaced with fresh reagents and the procedure for flushing the water standard lines and determining the water standard moisture content is repeated.

Once the system has passed system suitability, residual moisture is removed from the sample reservoir 28, which is a large length of coiled Teflon tubing 44 with about 7 ml of capacity, and the larger (10 ml) titrant syringe pump 30 used to process a sample in a like manner to that used for the water standard, above. When the moisture level of these lines 44, reservoir 28, and syringe pump 30 meet the 8.0 micrograms cut off, the sampling/dispensing probe 46 (FIGS. 2 and 3) is rinsed with 6 ml of dried titrant maintained in sample/titrant reservoir 28, which then goes to a waste reservoir in the autosampler 20, and the sample processing begins. Rinsing the sample probe 46 with titrant is important to prevent moisture from adhering to the probe and contaminating the sample in the steps that follow.

The titrant/sample syringe pump 30 then fills with dried titrant taken from the reaction vessel 38 of the Karl Fischer titrator up to the amount of titrant appropriate for the size of sample container 40 and the size of the solid sample plug 54. The probe assembly 26 is retracted from the titrant wash reservoir on the autosampler 20, is positioned over the sample 40 in tile sample rack 24 by the autosampler 20, and the sampling/dispensing probe 48 and vent tube 42 then puncture the sealed sample container 40 through metal cap 52 and the rubber septum 50 of the sample container 40 (FIG. 3). The 3-way valve 22 mounted on the autosampler 20 is then activated, which allows the appropriate volume of titrant 56 in the titrant/sample syringe pump 30 to be directed into the sample container 40 via two 1.6 mm probe holes 46 in sampling/dispensing probe 48 to dissolve the solid sample plug 54. The sample/titrant solution is mixed by drawing a portion of the solution out of the sample container 40 and into the sample reservoir 28, and then forcing this portion of sample/titrant solution back into the sample container 40, using the titrant/sample syringe pump 30 for both operations. This mixing procedure is repeated three times before a portion of the sample/titrant solution is withdrawn for titration from the sample container 40 and transferred into the sample reservoir 28. The 3-way valve 22 is deactivated, and an aliquot portion of the sample/titrant solution is carried into the reaction vessel 38 with about 6 ml of titrant delivered by titrant/sample syringe pump 30. The amount of moisture in the aliquot portion of the sample/titrant solution is then determinated by the Karl Fischer titrator, and the percent moisture is calculated, taking into account the sample size and the portion of the sample titrated.

At the end of the sample runs, another water standard is run, which allows the samples to be bracketed by water standards to assure proper system suitability. The results of the moisture content determinations for the samples and water standards are then sent to a printer or may be saved to disk.

Because of the limited volume of cartridges, they are treated differently than vials. Instead of delivering a single portion of coulomat solution to dissolve the solid sample plug 54, cartridges are dissolved by repetitively adding dried coulomat solution. The dissolved portion is then withdrawn and pushed into the reaction vessel 38. This process is repeated until the entire contents of the cartridge are transferred to the reaction vessel 38.

Optimization of Automated Process

In developing the automated Karl Fischer titration system, there were many experimental factors with several settings from which to choose. Therefore, optimization was needed. Twelve factors were identified that were believed could have an effect on the moisture content values. These factors included both instrumental parameters and reagent choices that also needed to be optimized.

The large amount of factors made it difficult to optimize each of them individually. Thus, the use of experimental design techniques were employed. These experimental design techniques were designed to provide the most information with relatively few experimental trials. To optimize the twelve key factors in the preferred embodiment, the Plackett-Burman experimental design was chosen. In this design, extreme high and low settings were chosen for each factor, which allowed for the determination of which of the 12 factors identified have a significant effect. If neither the high nor low value had an effect, than that particular factor did not need to be controlled. This allows factors that do not influence the results to be set at a value that may benefit a factor that does have an effect on the responses. The two responses that were monitored as factors were varied were moisture content of 5 mg of an hGH vialed material, and analysis time. Table I lists the 12 factors that were varied in the design experiment, the definition of each, and the high and low values for each parameter. Some of these factors, such as probe size or commercial titrant, allowed for only two choices. Other factors, such as relative humidity or stirring rate, had many values of the high/low value extremes.

TABLE I
Factors and High/Low Values for Plackett-Burman Design for Automated Karl Fischer Moisture System

| Factors | Definition | High Value | Low Value |
|---|---|---|---|
| Dispensing Rate (RATE) | Rate at which titrant is dispensed into sample container | 40 ml/min | 1.0 ml/min |
| Mixing Cycles (CYCLE) | Number of cycles that solution is drawn up into resevoir line and re-dispensed into sample container | 3 | 1 |
| Solubility Additive (FORMA) | Formamide added to titrant (6%) to help solubilize the sample | Yes | No |
| Probe Size (PROBE) | Size of probe used in dispensing/sampling of titrant/sample | ID 20 guage OD 16 guage | ID 22 guage OD 18 guage |
| Sensitivity Setting (SENSI) | Sensitivity of titrator setting to reach reaction endpoint | High | Low |
| Stirring Rate (STIR) | Revolutions per minute of stir bar in titration vessel | 700 | 70 |
| Titrant Added to Sample (ADDED) | Volume of titrant added to sample container | 5.3 ml | *3.4 ml |
| Sample Dispensed (SOLN) | Volume of sample added to reaction vessel | 4.0 ml | 1.0 ml |
| Humidity (HUMID) | Relative humidity inside the glove box | 25% | 5% |
| Commerial Titrant (TITRT) | Type of commercial titrant | Hydranal | Aquastar |
| Volume in Vessel (VOLUM) | Volume of titrant in the reaction vessel initially | 200 ml | 100 ml |
| Drawing Rate (DRAW) | Rate at which sample is drawn-up into the the reservoir line from the sample container | 40 ml/min | 1.0 ml/min |

*Low setting will be 5.3 ml when SOLN = 4 ml.

Having identified the 12 factors that would be varied and the two responses to be monitored, the experimental design trials were determined. Table II lists the 20 trials that were performed, with the high/low value for each factor and the percent moisture content and analysis time results for each trial.

long period of time to reach the titration endpoint, and could easily be picked up from the trial results. A bigger concern was the optimization of factors to eliminate low moisture content values due to incomplete mixing of the material. A low analysis time response was taken as the optimum value. This would indicate quick titration of the material resulting in faster throughput of samples. The results of trial 19 were omitted from the

TABLE II
Results of Placket Burman Experimental Design.

| Trial | DISPN | CY-CLE | FOR-MA | PRO-BE | SENSI | STIR | ADD-ED | SOLUT | HU-MID | TITRA | VOLUM | DRAW | Percent Water | Analysis Time (sec) |
|---|---|---|---|---|---|---|---|---|---|---|---|---|---|---|
| 1 | H | L | L | L | L | H | H | L | H | H | L | L | 0.3% | 40 |
| 2 | L | L | H | H | L | H | H | L | L | H | H | H | 0.6% | 55 |
| 3 | L | H | L | L | L | L | H | H | L | H | H | L | 0.2% | 75 |
| 4 | L | H | H | L | L | H | H | H | H | L | H | L | 0.5% | 125 |
| 5 | L | H | H | L | H | H | L | L | H | H | H | H | 0.6% | 170 |
| 6 | L | L | H | H | H | H | *L | H | L | H | L | L | 0.6% | 270 |
| 7 | H | H | H | L | H | L | H | L | L | L | L | H | 1.2% | 390 |
| 8 | H | H | L | L | H | H | H | H | L | H | L | H | 0.4% | 290 |
| 9 | H | H | L | H | H | L | *L | H | H | L | L | H | 0.4% | 90 |
| 10 | H | H | L | H | H | L | *L | H | H | H | H | L | 1.0% | 820 |
| 11 | H | H | H | H | L | H | *L | H | L | L | L | L | 0.4% | 90 |
| 12 | H | L | H | L | L | L | *L | H | H | L | H | H | 0.2% | 80 |
| 13 | H | L | H | H | L | L | H | H | H | H | L | H | 0.4% | 75 |
| 14 | L | H | L | H | L | L | L | L | H | H | L | H | 0.4% | 50 |
| 15 | H | L | L | H | H | H | H | L | H | L | H | L | 1.9% | 645 |
| 16 | H | H | L | H | L | H | L | L | L | L | H | H | 0.1% | 700 |
| 17 | L | L | L | H | H | L | H | H | L | L | H | H | 1.5% | 910 |
| 18 | H | L | H | L | H | L | L | L | L | H | H | L | 0.4% | 135 |
| 19 | L | H | H | H | H | L | H | L | H | L | L | L | 4.9% | 2400 |
| 20 | L | L | L | L | L | L | L | L | L | L | L | L | 0.1% | 30 |

The high/low settings were randomized for each trial to eliminate any experimental bias. These results were then computer analyzed to determine which factors were significant and whether a factor had a positive or negative effect on the response. A high moisture content response was taken as an optimum value. The two reasons for erroneously high moisture content values were environmental moisture contamination and/or computer analysis due to unrealistic numbers obtained for percent water and analysis time. These results were felt to be largely a result of the combination of high sensitivity setting and Aquastar titrant that resulted in an unusually long time to reach the reaction endpoint. The results of the computer analysis are listed in Table III, which lists the factors that had a significant effect and which factors settings were chosen and a brief rational behind the final settings.

TABLE III

Perfered Setting for Automated Karl Fischer System

| Factor | Preferred Setting – Percent Moisture | Preferred Setting – Analysis Time | Comments |
|---|---|---|---|
| Dispensing Rate | Neither | Neither | Set at 40 ml/min to maximize solution mixing |
| Mixing Cycles | Neither | Neither | Set at three cycles to maximize solution mixing |
| Formamide Added | High | Neither | Optimum concentration studies are shown in Table V |
| Probe Size | High | Low | Large hole size used to minimize possibility of clogging |
| Sensitivity Setting | High | Low | Low setting used to minimize time needed to reach endpoint |
| Stirring Rate | High | Neither | Set at high setting to miximize sample reaction time |
| Titrant Added | Low | Neither | Set at high value to take advantage of high "solution added" factor value |
| Solution Added | High | Neither | Set at 3.4 ml to maximize sample size and data precision |
| Humidity Setting | Neither | Neither | System is not effected by atmospheric humidity. Will set at 5% relative humidity to decrease atmospheric moisture contamination during non-use |
| Titrant Make | Low | Neither | Hydral will be used due to superior equilibrium time and equipment compatibility |
| Vessel Volume | Neither | Low | Set at 150 ml to account for volume lost during full run not sinking below eletrode |
| Drawing Rate | Neither | Neither | Set at 5 ml/min to minimize air in lines due to turbulence |

Several of the final settings deserve comment.

Humidity Setting

Neither a high nor a low humidity setting had an effect on the moisture content value. This indicated that the system of the preferred embodiment was air tight and that the glove box was not needed for the accurate measurement of moisture content in the sample containers 40. The controlled low humidity environment of the glove box, however, provides a low humidity chamber when the system is not in use. This lessens the amount of moisture entering the sample transfer lines 44 (28) and minimizes the time required to flush the transfer lines before analysis.

Volume of Titrant

The design experiment results indicated a low value (100 ml) is favored. The smaller volume results in fast analysis times, presumably due to optimum contact of moisture with the reaction chamber 38 electrode. The 100 ml volume level, however, would result in the titrant level falling below the level of the electrode when the sampling rack was fully loaded. A more appropriate volume is 150 ml, which allows for loss of titrant due to the flushing of the transfer lines 44 (28) and probe assembly 26, and the sample solution not transferred from the vials 40 when the sampling rack is fully loaded.

Commercial Titrant

Figure 4:
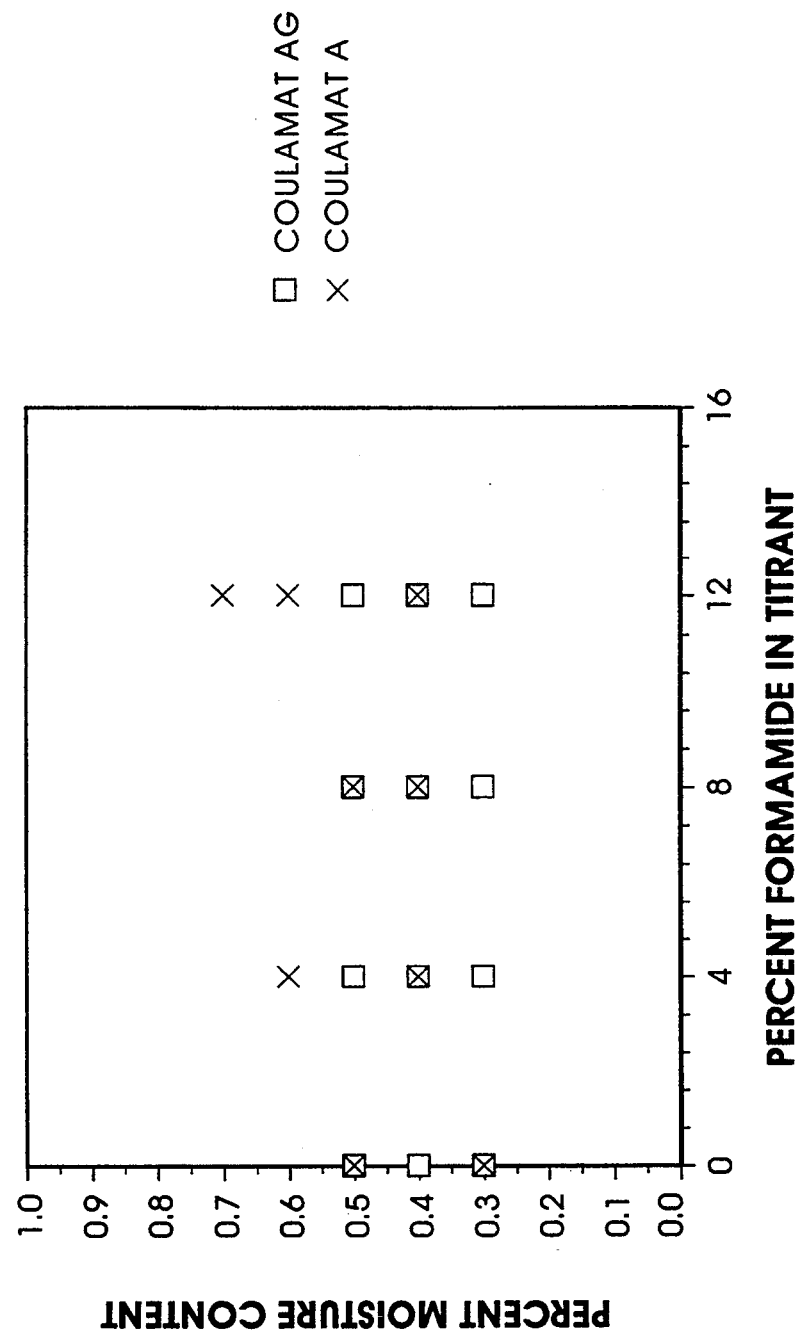
FIG. 4 is a graphic representation of an equivalency study using Coulomat A and AG titrants, illustrating the effect of titrant and percent formamide on percent moisture content in hGH formulations.

The design experiments favor the use of Aquastar titrant, but Hydranal® provides a preferable short equilibration time. In the process of developing and validating the automated system of the preferred embodiment, the future availability of Coulomat A came into question. Due to environmental concerns regarding the use of chloroform, the current titrant containing chloroform (Coulomat A) was replaced with Coulomat AG. Coulomat A and AG contain methanol, hydroiodic acid, and imidazole, but trichloromethane and sulfur dioxide in Coulomat A are replaced with diethanolamide-sulfite in Coulomat AG. The effect of this new titrant on moisture content values was studied to determine 1) the equivalence of Coulomat A to Coulomat AG, and 2) the effect of varying concentrations of formamide on either titrant. FIG. 4 shows the equivalency study using Coulomat A and AG showing the percent moisture content values in 5 mg hGH vials and $\mu g$ titrated in the water standard for both Coulomat A and AG as a function of percent formamide in the titrant. Up to a formamide concentration of 8%, there was little difference between the hGH formulation moisture content results using either Coulomat A or Coulomat AG. At 12% formamide, the hGH formulation moisture content value was slightly higher using Coulomat AG The solutions at 0% and 4% formamide using Coulomat AG were cloudy, although this physical difference did not show up in the moisture content results. From this study, it was determined that a formamide concentration of 8% gave the best results for the hGH formulation and that either Coulomat A or Coulomat AG may be used as the titrant, but due availability and environmental concerns Coulomat AG is preferred.

Calibration of Instrument/System Suitability

To get away from the various limitations associated with the commercial water standards or the volumetric inaccuracies of dispensing water by micro-syringe, a fixed loop design was used in the automated system as described above. Using two syringe pumps, the loop is filled with water and dispensed into the titrator by pushing 2.5 ml of dry titrant behind it. Sample loops of 0.5 $\mu l$ and 1.0 $\mu l$ were employed and gave average value of 706 $\mu g$ and 1206 $\mu g$ respectively. The run to run RSD was 0.5% for the 0.5 μg loop and 1.0% for the 1.0 μl loop. The additional 206 μg of moisture seen with each of the sample loops is consistent with the 0.2 μl dead volume estimated for injection valve 36 of the preferred embodiment (Model 7410, Rheodyne, Inc., Cotati, CA) by the manufacturer. Table IV lists the results of the accuracy and precision for the fixed loop system along with those obtained for the water dispensed into the titrator using a micro-syringe and four commercial water standards (two liquid and two solid water standards). These results are compared to the manufacturer's expected value for each and the percent gain in moisture content upon storage in a desiccator over a 45 day period.

good fit between the amount of water in the spiked sample and the moisture content determined by the automated system. The high accuracy of this instrument in determining the moisture content in these samples is also well demonstrated by the excellent fit of this data. The linearity over the entire range of spiked samples indicates that there is no problem in determining the amount of moisture in any size of the hGH formulations. The y-intercept, indicating no water added to the sample vial, for the spiked curve is 89.3 μg. This corresponds to a percent moisture content of 0.4% which matches well with the value determined for hGH samples, indicating a good fit in linearity over the entire moisture range.

TABLE IV

Water Standards for the Determination of System Suitability

| Standard | Actual Value | Expected Value | Difference (Actual vs. Expected) | Run to Run RSD | Day to Day RSD | 45 Day Moisture Increase |
|---|---|---|---|---|---|---|
| Water (0.5 μl loop) | 706 μg | 700 μg | 1% | 0.5% | 1.0% | 0% |
| Water (1.0 μl Delivered by Syringe) | 1044 μg | 1000 μg | 4% | 5% | 5% | 0% |
| Water in 2-methoxyethanol (Aquastar Water Standard) | 0.14% | 0.10% | 33% | 5% | 5% | 7% |
| Hydranal Check Solution | 0.11% | 0.10% | 14% | 0.5% | 3% | 7% |
| Hydranal Standard (Sodium tartrate-2-hydrate) | 14.3% | 15.7% | −9% | 1% | 4% | 7% |
| Lactose (Aquastar Solid Standard) | 4.8% | 5.0% | −4% | 1% | 3% | 2% |

Validation of System

The linearity, range, and accuracy of the automated system was determined by spiking 5 mg vials of hGH with water standards to determine the usefulness of the automated system over the range of sample sizes that would be analyzed. For spiked samples below a water content of 100 μgs, the samples were spiked with Hydranal ® Check Solution water standard contain 0.12% water as determined by Karl Fischer titration (Table IV). For spiked samples above 100 μgs, water was used. The water and water standard were added to the sample through the rubber septum using a syringe with the amount added determined by weight.

Figure 5:
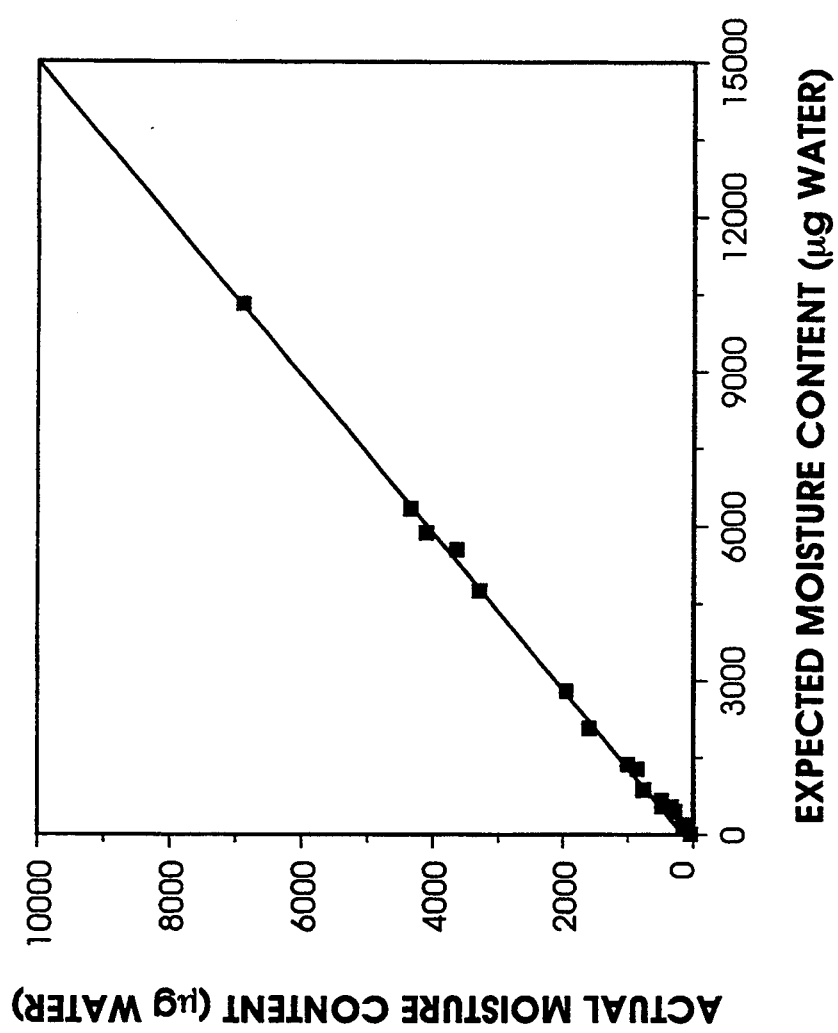
FIG. 5 is a graphic representation of the results of the moisture determination of 32 vials of hGH spiked with various amounts of water, and 4 vials without spiked water.

FIG. 5 shows the results of the moisture determination of 32 vials of hGH spiked with various amounts of water along with 4 vials where no water was added. The high water content spiked sample corresponds to a percent moisture content that is 500% larger than what would be reasonably expected from the largest hGH material size. The spiked sample data clearly brackets the amount that would be determined in the hGH formulations. The linearity of the data has a high correlation coefficient of 0.999 indicating that there is a very Comparison of Automated System with Prior Art Systems The moisture content of lyophilized hGH formulations of 5 mg vials was analyzed using three separate Karl Fischer systems: 1) a commercial Karl Fischer titrator exposed to the laboratory atmosphere, 2) a commercial Karl Fischer titrator (along with a balance) inside a controlled humidity environment of 104 relative humidity, and 3) the automated Karl Fischer titration system with the settings described in Table III. For instrument #1 and #2, the sample and vial were weighed, dispensed, and the empty vial reweighed to determine material dispensed. For instrument #3, the sample was dissolved in the titrant and dispensed into the titrator as described above. Table V lists the average moisture content values for each of the instruments over a three day period with the run to run and day to day confidence ranges for each.

TABLE V

Comparison of Three Karl Fischer Systems in the Moisture Content Determination of 5 mg Vialed hGH Formulation

| Karl Fischer System | Average Moisture Content | 95% Confidence Range (Run to Run) | 95% Confidence Range (Day to Day) |
|---|---|---|---|
| Instrument #1 (Exposed to Laboratory Humidity of 42–46%) | 1.3% | 0.3% to 2.3% | 0.7% to 1.9% |
| Instrument #2 (Controlled Humidity Environment of 10%) | 0.7% | 0.2% to 1.0% | 0.3% to 1.1% |
| Instrument #3 (Automated Titration System) | 0.6% | 0.4% to 0.8% | 0.4% to 0.8% |

Figure 6:
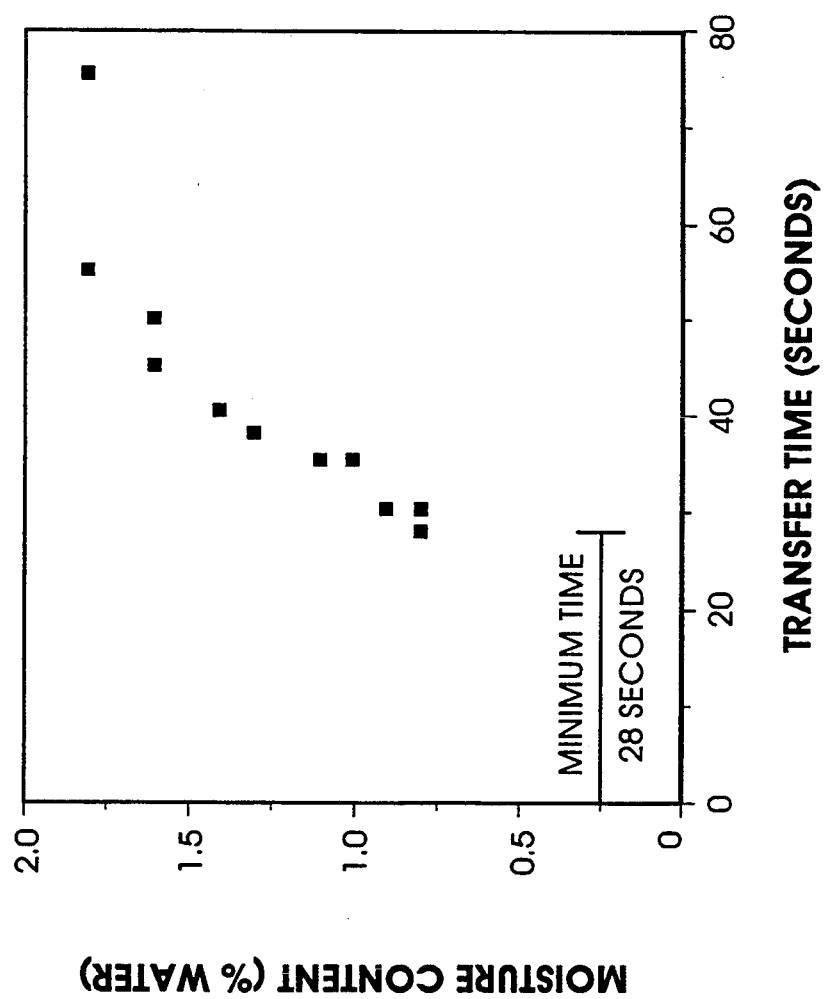
FIG. 6 is a graphic representation of the effect of sample handling in prior art methods upon moisture content of the samples.

The results from the automated system (instrument #3) were found to give the lowest moisture content results and the most narrow range. Again, it is noted that it was determined from the experimental design results that the relative humidity inside the glove box has no effect on moisture content. The titrator in the controlled environment of 10% humidity (instrument #2) gave results slightly higher than instrument #3, which may be a result of the humidity setting in the glove box (10%). This humidity may be higher than that of the closed vial, and moisture contamination from the atmosphere could occur. The precision of instrument #2 was found to be less than instrument #3 as indicated by the significant widening of run to run and day to day confidence range for instrument #2. As expected, instrument #1 gave the highest results, which is consistent with those finding above from contamination from the laboratory environment during sample transfer. The relative humidity varied between 42 and 46% during the three days of the study which resulted in significant moisture content gain in the sample. The run to run and day to day confidence ranges for instrument #1 is extremely large. This low precision is presumably due to the influence of moisture content on sample handling (time to transfer material) as shown in FIG. 6.

The automated Karl Fischer system of the present invention allows for the accurate, precise determination of moisture content in all sizes of hGH formulations (4 IU, 16 IU & 5 mg vials and 18, 36, & 72 IU cartridges). This system utilizes a two-hole sampling probe/venting needle that dispenses titrant and samples solution through the closed container septum, thus eliminating errors due to sample transfer and/or environmental moisture contamination. This system is also equipped with a fixed loop valving system to measure a defined amount of water. This allows for an accurate accessment of system suitability that was lacking with commercial water standards due to moisture contamination under storage and/or at the time of manufacture. The accurate determination of moisture content will facilitate a more complete understanding of the role of moisture content of hGH stability and if steps must be taken to better control the freeze-drying process. It is envisioned that this technology will quickly spread to other pharmaceuticals where moisture content plays a key role in product stability.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus for automated coulometric determinations of moisture content using a titration vessel connected to a coulometric analyzer, comprising:

a titration vessel connected to a coulometric analyzer, and having a reaction chamber containing titrant;

an autosampler having a sample rack for receiving sealed sample containers containing titrant soluble samples, sampling and dispensing probe means for piercing said sealed sample containers and for communicating titrant to and sample and titrant solutions from within sealed sample containers, and first automated 3-way valve means in fluid communication with said reaction vessel, with a sample and titrant reservoir, and with said probe means, for directing the flow of fluids alternatively between said probe means and said sample and titrant reservoir, and between said sample and titrant reservoir and said reaction chamber;

a first automated syringe pump in fluid communication through second automated 3-way valve means alternatively with said sample and titrant reservoir and said reaction chamber;

automated 4-port injection valve means in fluid communication with said reaction chamber, including a microliter loop of predetermined volume, for directing the flow of titrant through the microliter loop alternatively to or from said reaction chamber and to a waste reservoir, and for directing the flow of a liquid water standard alternatively from a liquid water standard source to said microliter loop and from said microliter loop to said reaction chamber;

a second automated syringe pump in fluid communication through third automated 3-way valve means alternatively with said microliter loop of said automated 4-port injection valve means and with said water standard source;

a third automated syringe pump in fluid communication through fourth automated 3-way valve means alternatively with said reaction chamber through said microliter loop of said automated 4-port injection valve means, and said waste reservoir; and computer means for controlling and coordinating the operations of said titration vessel and coulometric analyzer, said autosampler, said automated 4-port injection valve means, said first, second, third, and fourth automated 3-way valve means, and said first, second and third automated syringe pumps.

2. The apparatus of claim 1 and further comprising:

a hermetically sealed glove box encapsulating said titration vessel and coulometric analyzer, said autosampler, said automated 4-port injection valve means, said first, second, third and fourth automated 3-way valve means, and said first, second and third automated syringe pumps; and humidity control means for establishing and maintaining a relative humidity of less than about 10% within the glove box.

3. An apparatus for automated coulometric determinations of moisture content using a titration vessel connected to a coulometric analyzer, comprising:

a titration vessel connected to a coulometric analyzer, and having a reaction chamber containing titrant;

an autosampler having a sample rack for receiving sealed sample containers containing titrant soluble samples, sampling and dispensing probe means for piercing said sealed sample containers and for communicating titrant to and sample and titrant solutions from within sealed sample containers, and first automated 3w-ay valve means in fluid communication with said reaction chamber of the Karl Fischer, with a sample and titrant reservoir, and with said probe means, for directing the flow of fluids alternatively between said probe means and said sample and titrant reservoir, and between said sample and titrant reservoir and said reaction chamber;

a first automated syringe pump in fluid communicating through second automated 3-way valve means alternatively with said sample and titrant reservoir and said reaction chamber;

computer means for controlling and coordinating the operations of said titration vessel and coulometric analyzer, said autosampler, said first and second 3-way valve means, and said first automated syringe pump.

4. The apparatus of claim 3, and further comprising:
a hermetically sealed glove box encapsulating said titration vessel and coulometric analyzer, said autosampler, said first and second 3-way valve means, and said first automated syringe pump; and
humidity control means for establishing and maintaining a relative humidity of less than about 10% within the glove box.

* * * * *